United States Patent [19]

Tweedle et al.

[11] Patent Number: 5,468,467
[45] Date of Patent: Nov. 21, 1995

[54] METHODS FOR THE IN VIVO MEASUREMENT OF THE CONCENTRATION OF NON-IMAGING NMR-DETECTABLE XENOBIOTIC COMPOUNDS

[75] Inventors: Michael F. Tweedle, Princeton; Harry W. Strauss, Skillman; Adrian D. Nunn, Ringoes, all of N.J.

[73] Assignee: Bracco International B.V., Amsterdam, Netherlands

[21] Appl. No.: 52,959

[22] Filed: Apr. 23, 1993

[51] Int. Cl.$^6$ .................................................. A61B 5/055
[52] U.S. Cl. .................. 424/9.361; 436/173; 128/653.4; 128/654; 514/492; 514/502; 514/836; 424/9.363; 424/9.364
[58] Field of Search ................................ 424/9; 436/173; 128/653.4, 654; 514/836, 492, 502

[56] References Cited

U.S. PATENT DOCUMENTS

| | | | |
|---|---|---|---|
| 3,932,805 | 1/1976 | Abe et al. | 324/5 A |
| 4,885,363 | 12/1989 | Tweedle et al. | 540/465 |
| 4,984,573 | 1/1991 | Leunbach | 128/653 |
| 5,100,646 | 3/1992 | Choyke et al. | 424/9 |
| 5,190,744 | 3/1993 | Rocklage et al. | 424/9 |
| 5,234,680 | 8/1993 | Rogers, Jr. et al. | 424/9 |
| 5,248,498 | 9/1993 | Neomann et al. | 424/9 |
| 5,250,284 | 10/1993 | Krongrad | 424/9 |

OTHER PUBLICATIONS

Smith, W. B., "Nuclear Magnetic Resonance"; Enccyclopedia of Chemistry, pp. 732–736 (1973).
Battocletti, "Blood Flow Measurement by NMR"; CRC Critical Reviews in Biomedical Engineering, CRC Press Inc., vol. 13, Is. 4, pp. 311–367 (1986).
Salles–Cunha et al., "The NMR Blood Flowmeter–Applications"; Med. Phys. 8(4), pp. 452–458 Jul./Aug. (1981).
Battocletti et al., "The NMR Blood Flowmeter–Theory and History"; Med. Phys. 8(4), pp. 435–443, Jul./Aug. (1981).
Halbach et al., "The NMR Blood Flowmeter–Design"; Med. Phys, 8(4), pp. 444–451 Jul./Aug. (1981).
Malfertheiner et al., "NMR (Nuclear Magnetic Resonance)–A Non Intrusive Technique for Measurement of Blood Flow", vol. 6, No. 3, pp. 186–194, Sep. (1976).
Halbach et al., "Blood Flow Imaging Techniques Using of NMR"; IEEE 1982 Frontiers of Engineering in Health Care, pp. 557–560, Phila., PA, Sep. 20–21 (1982).
Tweedle, M. F., Work in Progress Toward Nonionic Macrocyhclic Gadolinium (III) Complexes; Contrast and Contrast Agents in Magnetic Resonance Imaging (Ed. Peter A. Rinck), pp. 65–73 (1988).
Ohgushi et al., "Dextran–Magnetite: A New Relaxation Reagent and Its Application to $T_2$ Measurements in Gel Systems", Journal of Magnetic Resonance, 29, pp. 599–601 (1978).
Choyke et al., "Hydrated Clearance of Gadolinium–DTPA as a Measurement of Glomerular Filtration Rate"; Kidney International, vol. 41, pp. 1595–1598 (1992).
Berthezene et al., Safety Aspects and Pharmacokinetics of Inhaled Aerosolized Gadolinium; Journal Magnetic Resonance Imaging, vol. 3, No. 1, pp. 125–130 (1993).
Tweedle, "Relaxation Agents in NMR Imaging"; J–C G. Bunzli and G. R. Choppin, Lanthanide Probes in Life, Chemical, and Earth Sciences, Chapter 5, pp. 127–179 (Elsevier, 1989).
Rubenstein, E., "Magnetic Resonance Imaging, Imaging with Photons"; Current Topics in Medicine (1988).
Armstrong et al., "Magnetic Resonance Imaging–Basic Principles of Image Production"; British Medical Journal, vol. 303, p. 35 (1991).
Armstrong et al., "Magnetic Resonance Imaging–Clinical Uses"; British Medical Journal, vol. 303, p. 105 (1991).
Shulman et al., "Nuclear Magnetic Resonance Spectroscopy in Diagnostic and Investigative Medicine", J. Clin. Invest., vol. 74, pp. 1127–1131 (1984).
Tweedle, M. F., "Gadolinium Chelates as Relaxation Agents in Magnetic Resonance Imaging", Journal of Alloys and Compounds, 180, pp. 317–323 (1992).
Tweedle, M. F., "Nonionic or Neutral?"; Radiology, vol. 178, No. 3, 891 (1991).
Ross et al., "Examination of a Case of Suspected McArdle's Syndrome By $^{31}$P Nuclear Magnetic Resonance"; The New England Journal of Medicine, vol. 304, No. 22, pp. 1338–1342 (1981).
S-E Bäck et al., "Contrast Media and Glomerular Filtration: Dose Dependence of Clearance for Three Agents", J. Pharm. Sci, 77, 765 (1988).
Scan Magazine, "Esaote builds unit to catch Niche MRI trend" (2 pages) and "[Metriflow pioneers trend to market niche MR]" (1 page) (1992).
Gaughan, G., "Nonionic Gadolinium Chelates"; *Enhanced Magnetic Resonance Imaging*, Contrast Media Principles, pp. 105–116, C. B. Mosby Co., edited by Val M. Rounge (1989).

Primary Examiner—Gary E. Hollinden

[57] ABSTRACT

Methods wherein the concentration of NMR-detectable xenobiotic compounds may be determined in living subjects by in vivo measurement of one or more magnetic resonance signals. In preferred embodiments, the present invention provides a method for evaluating, in vivo, the clearance rate of a xenobiotic compound from a living subject, thereby providing a noninvasive method for determining the status of the excretory organs of the subject, and a method for determining the proper dosing regimen of a pharmacologically active compound to be administered to the subject.

16 Claims, 4 Drawing Sheets

METHODS FOR THE IN VIVO MEASUREMENT OF THE CONCENTRATION OF NON-IMAGING NMR-DETECTABLE XENOBIOTIC COMPOUNDS

FIELD OF THE INVENTION

The present invention relates to methods wherein, by recording the intensity of one or more magnetic resonance signals obtained in vivo and comparison with the signal intensity of a standard, the concentration of an NMR-detectable xenobiotic compound may be determined in a living subject. In preferred embodiments, the present invention provides a method for evaluating, in vivo, the clearance rate of a xenobiotic compound from a living subject, thereby providing a noninvasive method for determining the status of the excretory organs of the subject, and a method for determining the proper dosing regimen of a pharmacologically active compound to be administered to the subject.

BACKGROUND OF THE INVENTION

The spinning of the nuclei of certain atoms such as $^1H$, $^{13}C$, $^{15}N$, $^{19}F$, $^{23}Na$, and $^{31}P$ generates a magnetic moment along the axis of spin. When placed in an external magnetic field, alignment with, or against, the magnetic field may result. Since alignment with the magnetic field is more stable, energy must be absorbed to excite the nucleus to the less stable alignment against the field. The frequency of the radiation energy required to excite a given nucleus is proportional to the strength of the external magnetic field; the stronger the magnetic field, the higher the frequency of the radiation required. When such nuclei return to their lower energy state, absorbed radiation is emitted, and a signal may be detected. Various analytical techniques utilize these magnetic resonance principles.

For example, nuclear magnetic resonance (NMR) spectroscopy has been employed to analyze the structure of chemical compounds. Generally, in this technique, the radiation frequency is kept constant, and the magnetic field strength varied. At some value of applied magnetic field strength, which value is characteristic of the type of nucleus and the environment in which it is found, the energy required to excite the nucleus matches the energy of the radiation, absorption occurs, and a signal may be observed. The number, positions and intensities of the signals obtained while varying the magnetic field strength are recorded as a nuclear magnetic resonance spectrum which provides detailed information on molecular structure. It has been reported by Shulman et al. that NMR spectroscopy has been employed in certain cases both in vitro and in vivo. (Shulman et al., "Nuclear Magnetic Resonance Spectroscopy in Diagnostic and Investigative Medicine", *J. Clin. Invest.*, Vol. 74, 1127–1131 (1984)). NMR spectroscopy, however, while capable of providing extensive information on compounds assayed, requires high field homogeneity across the sample in order to obtain accurate spectra, and a means of varying the magnetic field.

Other NMR techniques include magnetic resonance imaging (MRI), which has been used to study morphology in vivo. Generally, in this technique, the parameters governing the intensity of signals emitted by protons, such as the longitudinal relaxation ($T_1$) and transverse relaxation ($T_2$) times, are measured across a subject. Measurements are obtained by applying a magnetic field gradient, that is, a magnetic field the strength of which varies across the subject, and applying pulsed radiation energy. The magnetic field gradient allows data to be obtained which can be converted into two and three dimensional images. Especially when used in conjunction with compounds enhancing contrast such as by shortening $T_1$ ("contrast agents"), MRI provides clinically useful data, such as data allowing the detection of morphological abnormalities. To enable images of the subject to be obtained, however, MRI equipment is generally large and cumbersome, so that the technique is unsuitable for the determination of the concentration of xenobiotic compounds in settings such as a patient's room or a physician's office.

In vitro measurement of NMR $T_1$ relaxation times for the determination of glomerular filtration rate is described in Choyke et al., *Kidney International*, Vol. 41 (June 1992). In vitro testing, however, requires the sampling of body fluids such as blood and urine. Withdrawal and testing of such fluids adds time and expense to the evaluation of a patient, and is particularly undesirable from the standpoint of handling and sanitation.

SUMMARY OF THE INVENTION

The present invention provides a method for the non-spectroscopic, non-imaging determination in vivo of the concentration of an NMR-detectable xenobiotic compound, comprising the steps of:

(a) recording one or more in vivo measurements of the intensity of a magnetic resonance (NMR) signal from said xenobiotic compound at a measurement site of a living subject by employing an NMR detection system which is capable of measuring the intensity of said signal and which is located at said measurement site; and (b) determining the concentration of said xenobiotic compound by a comparison of the signal intensity of said one or more measurements obtained in step (a) with the signal intensity of a standard.

In preferred embodiments, the present invention provides a method for evaluating, in vivo, the clearance rate of a xenobiotic compound from a living subject, allowing determination of the status of the excretory organs, and a method for determining the proper dosing regimen of a pharmacologically active compound to be administered to the subject. Clearance rate may be determined by the measurement of signal intensity remote from the site of interest. Thus, for example, where excretory organ function is to be determined, the measurement site may be remote from the excretory organ(s).

The present invention further provides a method for the in vivo determination of the clearance rate of an NMR-detectable xenobiotic compound by one or more excretory organs of a living subject, comprising the steps of:

(a) recording one or more in vivo measurements of the intensity of a magnetic resonance (NMR) signal from said xenobiotic compound at a measurement site of said subject by employing an NMR detection system which is capable of measuring the intensity of said signal and which is located at a measurement site of said subject which is remote from said one or more excretory organs; and (b) determining the clearance rate of said xenobiotic compound by a comparison of the signal intensity of said one or more measurements obtained in step (a) with the signal intensity of a standard.

Where more than one measurement is recorded in step (a), continuous or periodic measurements (such as one, two or three times per day) may be taken.

The present invention thus provides a rapid, noninvasive method for measurement of the concentration of xenobiotic compounds in living subjects. As neither cumbersome equipment nor the sampling of body fluids are required, the present method provides advantages with respect to cost and sanitation, and is readily adapted to the clinical setting.

DETAILED DESCRIPTION OF THE INVENTION

Figure 1:
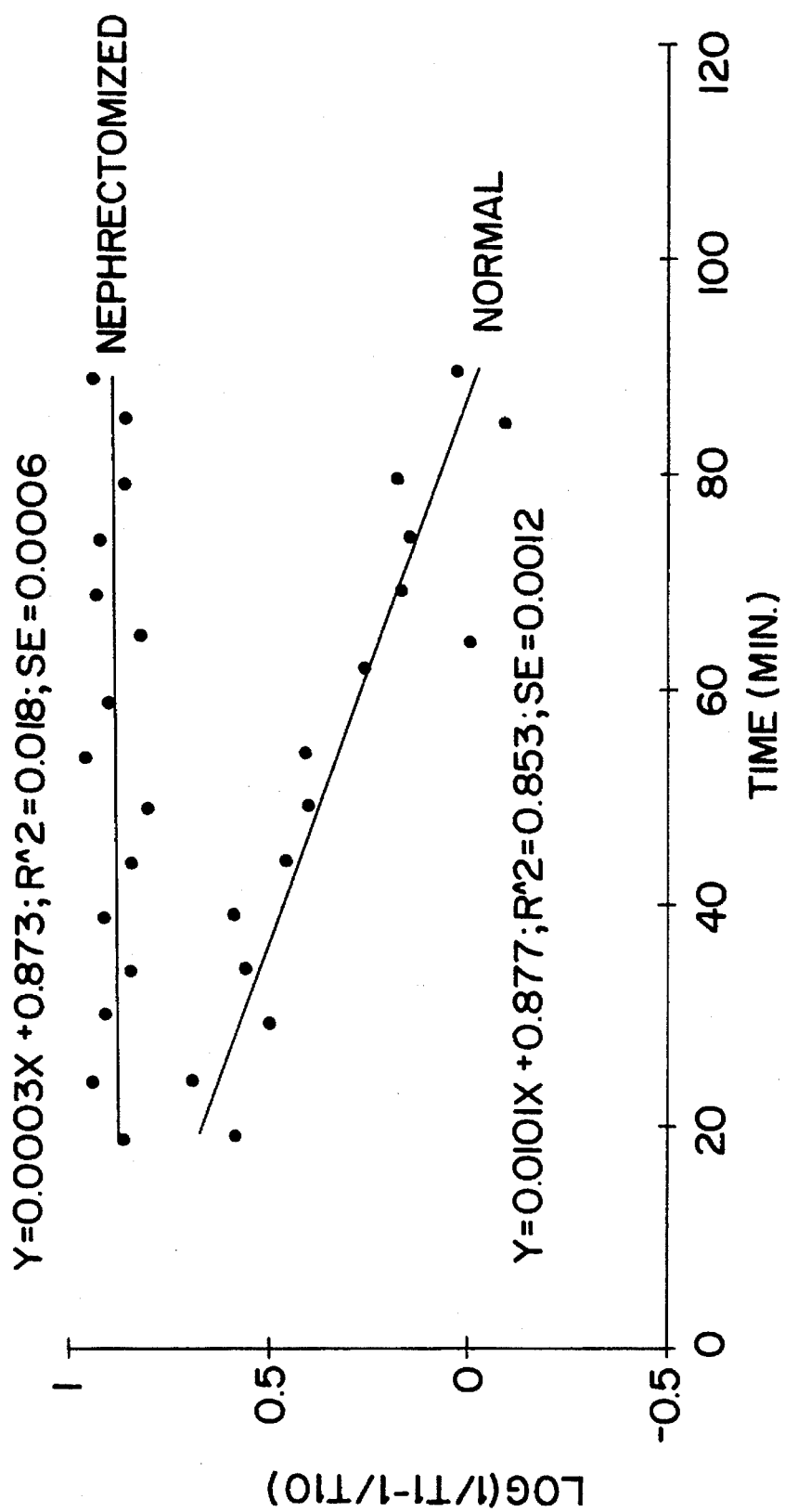
FIG. 1 shows proton $T_1$ data, measured at the tail of normal and nephrectomized rats injected with ProHance®. ProHance® is a paramagnetic xenobiotic compound which affects the $^1$H NMR signal from the rat tail.

The present invention is described in further detail as follows.

The term "NMR-detectable xenobiotic compound", as used herein, denotes any compound the presence of which may be detected by NMR in vivo, such as when administered to a living subject. Preferably, the NMR-detectable xenobiotic compound employed in the present method is a compound which is not found naturally in the living subject, although naturally occuring compounds may be administered, for example, to provide amounts in vivo in excess of those found prior to administration.

NMR-detectable xenobiotic compounds may be NMR-detectable per se by possessing an NMR-detectable nucleus such as $^1$H, $^{13}$C, $^{15}$N, $^{19}$F, $^{23}$Na, and/or $^{31}$P, or may be NMR-detectable by altering the signal from another compound possessing an NMR-detectable nucleus. Compounds possessing NMR-detectable nuclei per se are exemplified by pharmacologically active compounds containing an NMR-detectable nucleus such as 5-fluorouracil, a cancer chemotherapeutic agent; compounds detectable by their effect on the NMR-detectable nucleus of another compound are exemplified by contrast agents, which alter the relaxation times of the protons of water (for example, water molecules endogenous to a living subject), especially extracellular contrast agents.

The term "non-spectroscopic", as used herein with respect to an NMR detection method, refers to such a method wherein data are collected without obtaining a spectrum, such as data collection without substantially varying the magnetic field strength or radiation energy frequency over time. A "non-spectroscopic" method may thus consist essentially of an NMR detection method wherein a spectrum is not obtained.

The term "non-imaging", as used herein with respect to an NMR detection method, refers to such a method wherein data are collected without obtaining a two or three dimensional image, such as data collection without substantially varying the magnetic field strength spatially over the sample. A "non-imaging" method may thus consist essentially of an NMR detection method wherein an image is not obtained. The method of the present invention may further consist essentially of an NMR detection method wherein a flow measurement, such as a blood flow measurement, is not obtained.

According to the non-spectropic, non-imaging method of the present invention, each of the one or more measurements may be obtained, over time and space, at substantially the same magnetic field strength and substantially the same radiation energy frequency. The signals detected in step (a) may represent the sum total of the nuclei being analyzed.

The signal intensity of the "standard" of step (b) may be an in vivo measurement obtained either prior or subsequent to administration of the xenobiotic compound to the subject. Where, subsequent to administration of said xenobiotic compound, measurements are taken sequentially over time, each measurement may be treated, sequentially, as a measurement in accordance with step (a) and then, when a later measurement is taken, a standard in accordance with step (b). Thus, for example, by comparing, sequentially, measurements taken later in time with those taken earlier (each earlier value being a "standard" for the purposes of step (b)), the rate of clearance of the xenobiotic compound from the subject may be obtained. Although less preferred due to the potential variability between subjects, the "standard" may be a measurement taken prior or subsequent to administration of the xenobiotic compound to a different subject than that from which the measurement(s) of step (a) are taken (for example, to compare the clearance rate of the xenobiotic compound in a healthy subject against the clearance rate in a subject in which disease of the excretory organs is known or suspected).

"Concentration", as used herein, denotes relative or absolute concentration. Thus, "determining the concentration" in step (b), as used herein, encompasses determining the relative concentration of a xenobiotic compound, including determining the presence or absence of the compound or determining a relative change in the concentration of the compound over time (where, for example, signal intensity is proportional to the amount of the compound, and a difference is observed between the signal intensity of the standard and that recorded in step (a)); and determining the absolute concentration of a xenobiotic compound (where, for example, the function of absolute concentration of the compound, as determined by in vitro assay, versus signal intensity, as determined by in vivo measurement contemporaneously with withdrawal of the sample for in vitro assay, is plotted, and the step (a) measurement compared against the function obtained). The information obtained may thus be qualitative (for example, relative change in concentration over time) or quantitative in nature.

In one embodiment, the present invention provides a method for the non-spectroscopic, non-imaging determination in vivo of the concentration of an NMR-detectable xenobiotic compound, comprising the steps of:

(i) prior to administration of said xenobiotic compound, recording an in vivo measurement of the intensity of a magnetic resonance (NMR) signal from nuclei, such as $^1$H, endogenous to a living subject, at a measurement site of said subject, by employing an NMR detection system which is capable of measuring the intensity of said signal and which is located at said measurement site;

(ii) administering said xenobiotic compound to said subject, wherein said compound is capable of altering the intensity of the NMR signal from said endogenous nuclei;

(iii) subsequent to said administration, recording an in vivo measurement of the intensity of the NMR signal from said endogenous nuclei, the latter having been altered by the presence of said xenobiotic compound, by employing said NMR detection system; and (iv) determining the concentration of said xenobiotic compound by a comparison of the measurement obtained in step (i) with the measurement obtained in step (iii).

In this embodiment, the signal intensity of the "standard" is determined in step (i), and steps (iii) and (iv) correspond to steps (a) and (b), respectively, of the general method of the present invention.

In another embodiment, the present invention provides a method for the non-spectroscopic, non-imaging determination in vivo of the concentration of an NMR-detectable xenobiotic compound, comprising the steps of:

(i) administering said xenobiotic compound to a living subject, wherein said xenobiotic compound possesses an NMR-detectable nucleus per se or where said xenobiotic compound is capable of altering the intensity of a magnetic resonance (NMR) signal from nuclei endogenous to said subject;

(ii) subsequent to said administration, recording an in vivo measurement of the intensity of a magnetic resonance (NMR) signal generated by the NMR-detectable nuclei of said xenobiotic compound or generated by said endogenous nuclei, the latter having been altered by the presence of said xenobiotic compound, at a measurement site of said subject, by employing an NMR detection system which is capable of measuring the intensity of said signal and which is located at said measurement site;

(iii) thereafter, repeating step (ii) at least once at a time prior to complete clearance of said xenobiotic compound by excretion and/or metabolism from said subject; and (iv) determining the concentration of said xenobiotic compound, as a function of time, by a comparison of the measurement obtained in step (ii) with the measurement(s) obtained in step (iii).

In this embodiment, the signal intensity of the "standard" is determined in step (ii), and steps (iii) and (iv) correspond to steps (a) and (b), respectively, of the general method of the present invention.

The term "living subject", as used herein, preferably denotes a mammal such a cat, dog, horse or other domestic mammal, and most preferably denotes a human.

The "intensity of the NMR signal measured" may be expressed as any parameter derived from the formula:

$$\frac{d\rho}{dt} = i[H,\rho]$$

where $\rho$ is the density matrix describing the population of spin states in the system;

t is time;

H is the total spin hamiltonian for the system; and i denotes the square root of −1.

Exemplary such parameters include relaxation time $T_1$, relaxation time $T_2$, $T_{1\rho}$, $$\pi \sum_i^n I_z$$

(dipolar order), nuclei density, $K_n$, and other such NMR parameters. Measurement may be made by any suitable method, including pulsing or non-pulsing methods.

The xenobiotic compound may be administered orally, parenterally (for example, intravenously, intraparentoneally, intramuscularly, or subcutaneously), rectally, or by any other suitable method of introducing such a compound into a living subject, including inhalation (for example, inhalation of aerosolized gadolinium-containing compounds, such as by use of a jet nebulizer).

One preferred embodiment of the method of the present invention is the determination of the concentration of a pharmacologically active compound used for the treatment or prophylaxis of a disease condition in a living subject, especially to determine the proper dosing regimen thereof. Although dosing ranges for a species generally may be known or determined for such compounds, variation within a species may exist due, for example, to the sex, age and state of health of the subjects therein. Thus, a noninvasive method for determining the clearance rate based on excretion and/or metabolism over time for a particular subject is advantageous to avoid over- or under-dosing. In this embodiment, the xenobiotic compound may be any pharmacologically active compound which is NMR-detectable, such as $^{19}$F-containing pharmaceuticals including $^{19}$F-containing oncology pharmaceuticals exemplified by 5-fluorouracil and fluoro-taxol, $^{19}$F-containing antibiotics (e.g. antibacterials such as fluoro-quinolones), $^{19}$F-containing central nervous system (CNS) agents, for example, antidepressants such as Prozac® (fluoxetine hydrochloride) and antipsychotics such as fluphenazine, $^{19}$F-containing antiinflammatory agents such as fluperolone acetate and fluoromethalone, $^{19}$F-containing analgesics such as flupirtine and $^{19}$F-containing blood substitutes such as fluosol DA or perfluorooctyl bromide (PFOB) (the latter also useful as a contrast agent for monitoring lung and/or liver function), as well as other $^{19}$F-containing pharmaceuticals such as those listed in *The Merck Index* (1989); and $^{13}$C-containing compounds, such as any carbon-containing pharmaceutical, for example, diagnostic compounds such as $^{13}$C-containing iopamidol. An analogue of a pharmacologically active compound which is "tagged", that is, modified to contain an NMR-detectable component may also be employed.

In this embodiment, an NMR-detectable, pharmacologically active xenobiotic compound may be administered to a subject, and the concentration of that compound followed over time by the present method. The amount and timing of the dosage to be administered to a particular subject may then be adjusted, as appropriate, to maintain desired levels of the compound over the course of the treatment or prevention.

Another preferred embodiment of the present invention is that where the clearance rate (that is, whether or not clearance occurs, and preferably the decrease in the amount, relative or absolute, of the compound as a function of time) of a xenobiotic compound from a living subject is determined, providing information as to the functional status of the excretory organs of that subject such as the kidneys, liver and lungs. In this embodiment, for example, the absence of removal of the compound administered, or removal at a rate below that found in healthy subjects, assists in diagnosing dysfunction of the excretory organ, or in following the progress of disease in that organ. Xenobiotic compounds which may be employed in this embodiment are those cleared by the organ of interest, and which are preferably not metabolized to a substantial degree by the subject, or cleared concurrently by organs other than the organ or organs of interest.

In a particularly preferred embodiment of the method of the present invention, the glomerular filtration functioning of a living subject may be determined. Thus, for example, determining the halftime for glomerular filtration of a xenobiotic compound which is cleared through the kidneys by the present method allows evaluation of the health of these organs. An optimum xenobiotic compound to be employed in this embodiment is one which is substantially, preferably completely, removed from the subject through the kidneys, and which is preferably neither secreted nor reabsorbed by the renal tubules. Paramagnetic contrast agents are particularly useful in this regard, especially those which are chelates of gadolinium. Exemplary of the latter are Gd-diethylenetriaminepentaacetic acid (Gd-DTPA) (eg. Gd-DTPA disodium or dimeglumine salts), Gd-diethylenetriaminetriacetic acid bismethylamide (Gd-DTPA-BMA), and Gd-tetraazacyclododecane tetraacetic acid (Gd-DOTA), preferably gadoteridol, Gd-hydroxypropyl tetraazacylo dodecanetriacetic acid (Gd-HP-DO3A) (ProHance®). Such compounds are described, for example, in U.S. Pat. No. 4,885,363. The paramagnetic compound may be administered to the subject by any suitable route, preferably intravenously. Amounts employed should be suitable for detection, and may, for example, be 0.005 to 1, preferably 0.05 to 0.3 mmol/kg of contrast agent based on body weight.

An exemplary such method involves an initial in vivo measurement of relaxation time $T_1$ from a subject, followed by the administration of an NMR-detectable paramagnetic compound. Subsequent in vivo measurements of $T_1$ are then obtained over time, such as every 5 to 90 minutes following administration. The subject may void the compound via the kidneys during the study time.

The logarithms of the differences in the inverse of relaxation time $T_1$ before and after administration (that is, $\log(1/T_1 - 1/T_{10})$, where $T_1$ represents a relaxation time $T_1$ taken after administration and $T_{10}$ represents the relaxation time $T_1$ taken prior to administration) may be plotted as a function of time, and the elimination halftime ($T_{1/2}$) calculated from the slope of the log plot according to known methods (see N-E Back et al., *J. Pharm. Sci.,* 72, 765 (1988)). The halftime value(s) so obtained allow a diagnosis as to the glomerular filtration functioning of the subject, and hence an evaluation of the health of the kidneys of that subject. Glomerular filtration rates may be calculated from relaxation time data as described in Tweedle, "Relaxation Agents in NMR Imaging" in J-C. G. Bunzli and G. R. Choppin, Lanthanide Probes in Life, Chemical and Earth Sciences, Theory and Practice, Chapter 5, pp. 127– 179 (Elsevier, 1989).

Thus, the present invention provides a method for the non-spectroscopic, non-imaging evaluation in vivo of the glomerular filtration functioning of a living subject, comprising the steps of:

(i) recording an in vivo measurement of the intensity of a magnetic resonance (NMR) signal from nuclei endogenous to said subject, at a measurement site of said subject, by employing an NMR detection system which is capable of measuring the intensity of said signal and which is located at said measurement site, and calculating $T_{10}$, where $T_{10}$ is the longitudinal relaxation time corresponding to said measurement;

(ii) thereafter, administering to said subject a renally excreted contrast agent which is capable of altering the intensity of the NMR signal from said endogenous nuclei;

(iii) subsequent to said administration, recording one or more in vivo measurements of the intensity of the NMR signal from said endogenous nuclei, the latter having been altered by the presence of said contrast agent, by employing said NMR detection system and, for each measurement so obtained, determining $T_1$, where $T_1$ is the longitudinal relaxation time corresponding to each said measurement;

(iv) calculating the halftime $T_{1/2}$ from said values $T_{10}$ and $T_1$; and (v) evaluating the glomerular filtration of said subject from the value $T_{1/2}$.

The "measurement site" of the method of the present invention may be any part of the living subject which may be admitted to the sampling section of the NMR apparatus employed, and from which an in vivo measurement of the intensity of an NMR signal may be obtained. The measurement site may be remote, that is, physically distinct from, the site of interest. Thus, for example, glomerular filtration functioning may be determined by the use of an extremity as the measurement site. In this case, renal excretion may be reflected in a lowering of the concentration of the xenobiotic compound in the blood of the extremity. Preferred sites include an extremity such as an arm, most preferably, a finger or toe, or earlobe, of a human patient as such body parts, particularly the latter, are relatively small and therefore may be admitted to an NMR apparatus having a correspondingly small sampling section. In such cases, the size of the overall equipment required is minimized, allowing use of the present method at the bedside of a patient.

Bedside monitoring of xenobiotic compounds, such as contrast agents providing information as to the status of the excretory organs of the subject (e.g. glomerular filtration), provides advantages in the clinical setting. For example, seriously ill patients may be monitored without movement to a separate monitoring site, and the relatively small equipment is cheaper and more portable.

The NMR apparatus employed may be any apparatus containing a sampling section capable of admitting a part of the subject, and which is capable of measuring the intensity of an NMR signal. Exemplary such apparatus include NMR analyzers such as commercially available IBM or Bruker PC Series Spin Analyzers (e.g. PC10, PC20 and PC40 Spin Analyzers). The PC20 apparatus employed in the Examples herein operates at 20 MHz in a 0.5 Tesla magnetic field for the detection of $^1H$. (On an apparatus such as a PC10 or PC20, the platform above the sample well may be lowered to admit an extremity such as a finger.)

Exemplary magnetic field strengths which may be employed are those $\geq 0.02$ Tesla, preferably between about 0.1 and 0.5 Tesla, most preferably 0.5 Tesla. The homogeneity of the field strength is preferably selected to provide a detectable signal over background and noise, for example, from about 1 to 10 ppm. Radiation frequencies may be selected as appropriate for the nuclei to be detected. Exemplary radiation frequencies for the detection of $^1H$ at 0.1 to 0.5 Tesla fields are those between 4 and 20 MHz.

The present invention is illustrated further by the following Examples, which are in no way intended to limit the scope of the present claims.

EXAMPLE 1

To demonstrate use of the present invention for monitoring the kidney status of living subjects, rats were injected with ProHance®, and $T_1$, based on the interaction of ProHance® with water protons, was analyzed over time. The measurement site was the tail of the subject rat, which was hung into the sample tube of a Brucker/IBM PC 20 Spin Analyzer (commerically available).

Rat proton $T_1$ data were recorded both before and after intravenous injection of 0.5 mmol/kg ProHance®. The $T_1$ measurements were made by the inversion-recovery method (Fukushima et al., Experimental Pulse NMR, a Nuts and Bolts Approach (Addison-Wesley 1981)) at 20 MHz and 0.5 Tesla at 40° C. with the IBM PC 20 relaxometer by sampling the section of the rat tail about 10 mm from the tip. The proton $T_1$ change upon the injection of ProHance® was followed for 2 hours at 5 minute intervals after injection. The logarithms of the differences in the $T_1$ relaxation rate (reciprocal of $T_1$ relaxation time) before and after injection, $\log(1/T_1-1/T_{10})$, were plotted as a function of time. The elimination halftimes ($T_{1/2}$) were calculated from the slopes of the log plots. The results obtained are presented in Table 1. The proton $T_1$ data of a nephrectomized rat were also collected and used for comparison with the behaviour of normal rats (see FIG. 1).

Figure 2:
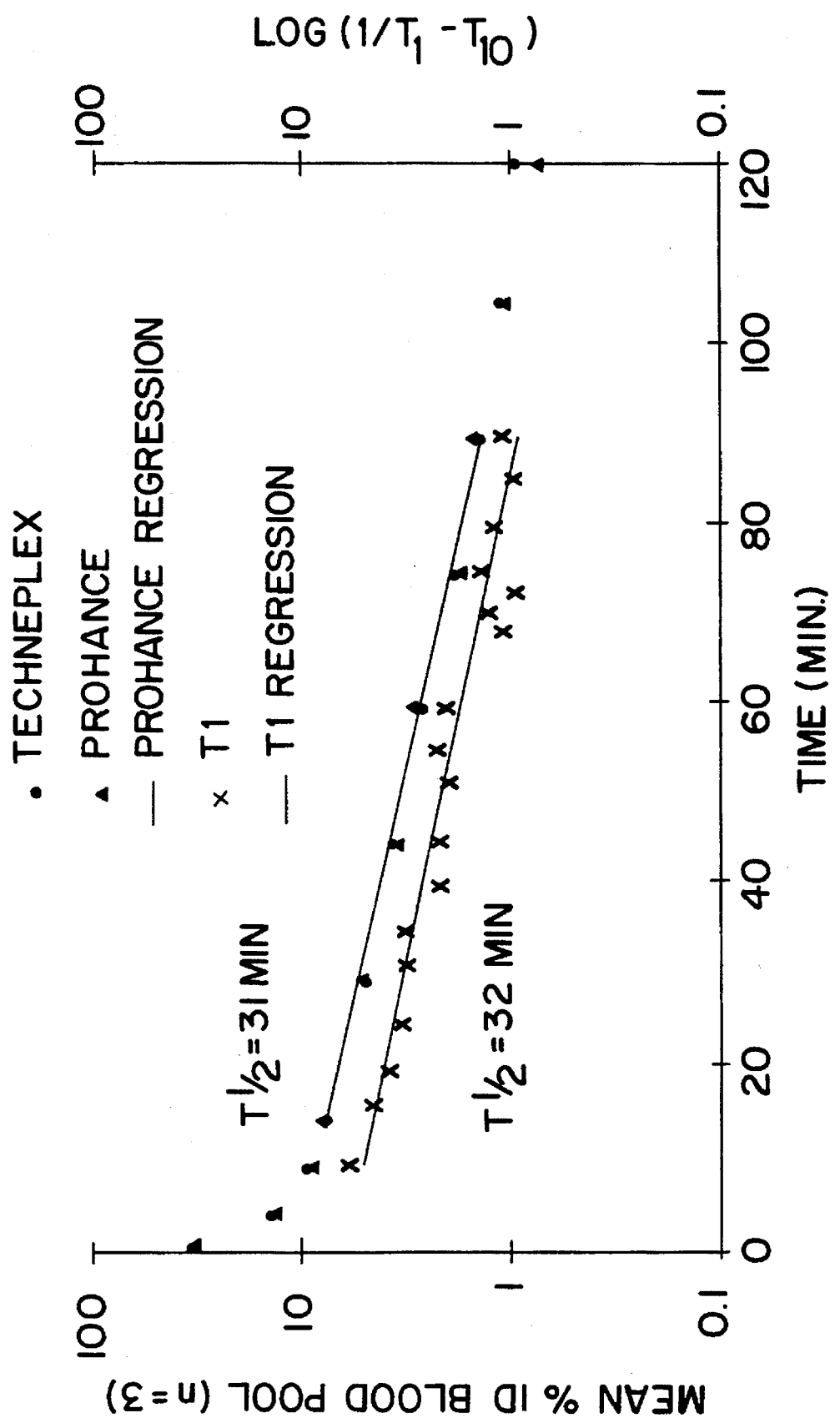
FIG. 2 shows proton $T_1$ data and mean % injected dose (ID) in blood pool for ProHance® and Techneplex™ in rat blood. Techneplex™ is a radioactive diagnostic agent which is excreted by glomerular filtration and may be used to assess renal function.

Runs involving simultaneous intravenous injection administrations of 0.5 mmol/kg ProHance®, $^{153}$Gd-labeled ProHance® and $^{99m}$Tc(DTPA) (Techneplex™, technetium-diethylenetriamine pentaacetic acid), the latter to determine glomerular filtration rate by in vitro methods as a validation experiment, were also carried out. In these runs, rat blood samples and tail $T_1$ data were acquired at the same time intervals from the same rat, and with multiple subjects (n=3). The blood samples were assayed in vitro to determine the amounts of $^{153}$Gd-labeled ProHance® and $^{99m}$Tc(DTPA) in the blood, and the percentage changes in the blood pool concentrations of $^{153}$Gd-labeled ProHance® and $^{99m}$Tc(DTPA) were plotted as a function of time to obtain the $T_{1/2}$ values. The $T_{1/2}$ data were also calculated from the slopes of the $\log(1/T_1-1/T_{10})$ versus time plots. These two sets of rat $T_{1/2}$ data are shown in Table 1, and are also compared in FIG. 2. The high level of agreement in $T_{1/2}$ values between the in vitro methods and the in vivo method of the present invention, as can be seen from FIG. 2, demonstrates the feasibility of the latter as a noninvasive NMR technique useful for examining glomerular filtration function, without requiring the undesirable handling precautions of radionuclide tracers, and without requiring blood or urine sampling.

TABLE 1

Elimination halftimes in rats after intravenous injection of 0.5 mmol/kg ProHance ®

| Rat Sample | Slope of Log $(1/T_1-1/T_{10})$ vs Time Plot | Elimination Halftime $T_{1/2}$ (min.) From Slope | From $^{153}$Gd and $^{99m}$Tc* |
|---|---|---|---|
| Nephrectomized | 0.0003 ± 0.0006 | 2,000 ± 4,000 | — |
| #1 | 0.012 ± 0.0020 | 25 ± 4 | — |
| #2 | 0.010 ± 0.0012 | 30 ± 3 | — |
| #3 | 0.0083 ± 0.0005 | 36 ± 2 | — |
| #4 | 0.015 ± 0.0016 | 20 ± 2 | — |
| #5 | 0.0093 ± 0.0006 | 32 ± 2 | 31 |
| #6 | 0.0087 ± 0.0012 | 35 ± 5 | 31 |
| #7 | 0.0093 ± 0.0006 | 32 ± 2 | 31 |

*same values obtained

EXAMPLE 2

Figure 3:
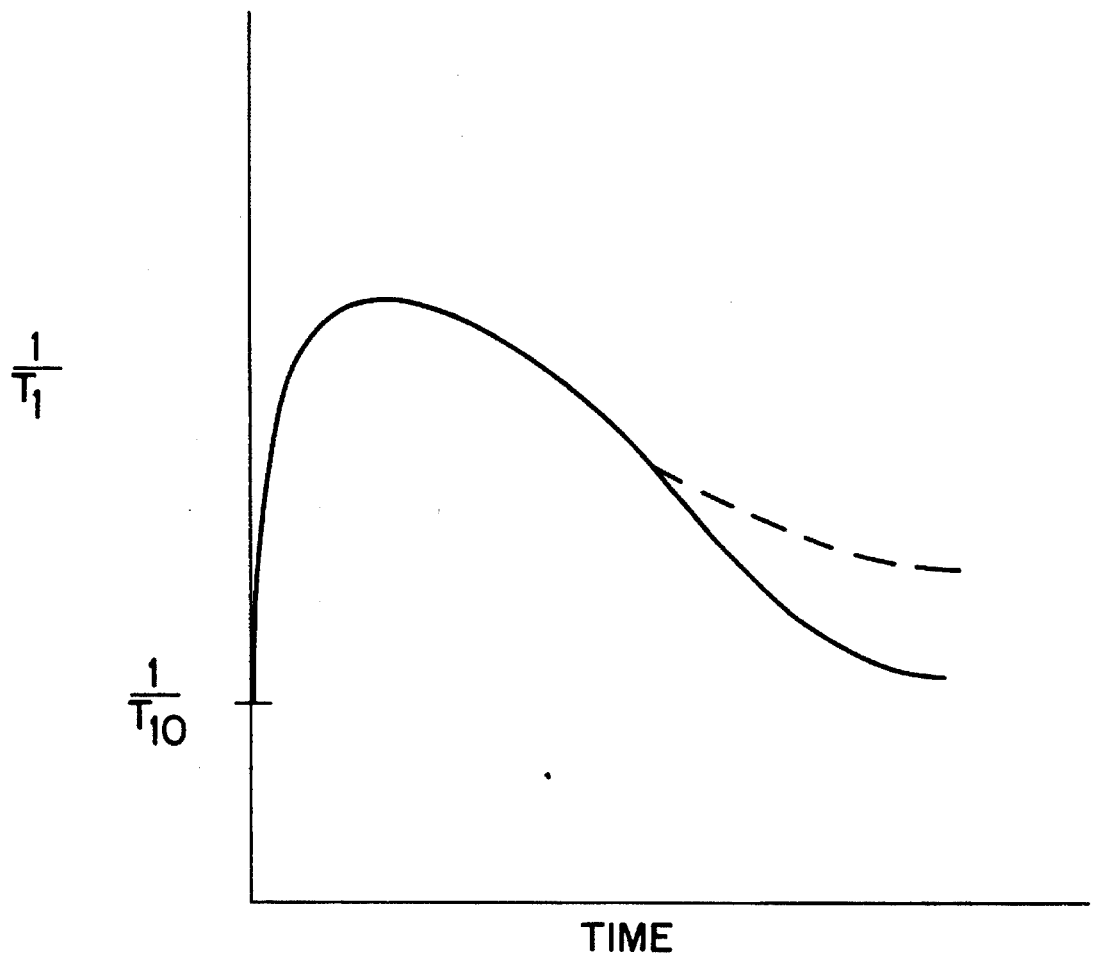
FIG. 3 shows the expected function of the inverse of relaxation time $T_1$ versus time for a patient administered a bolus injection of a renally excreted xenobiotic compound.
Figure 4:
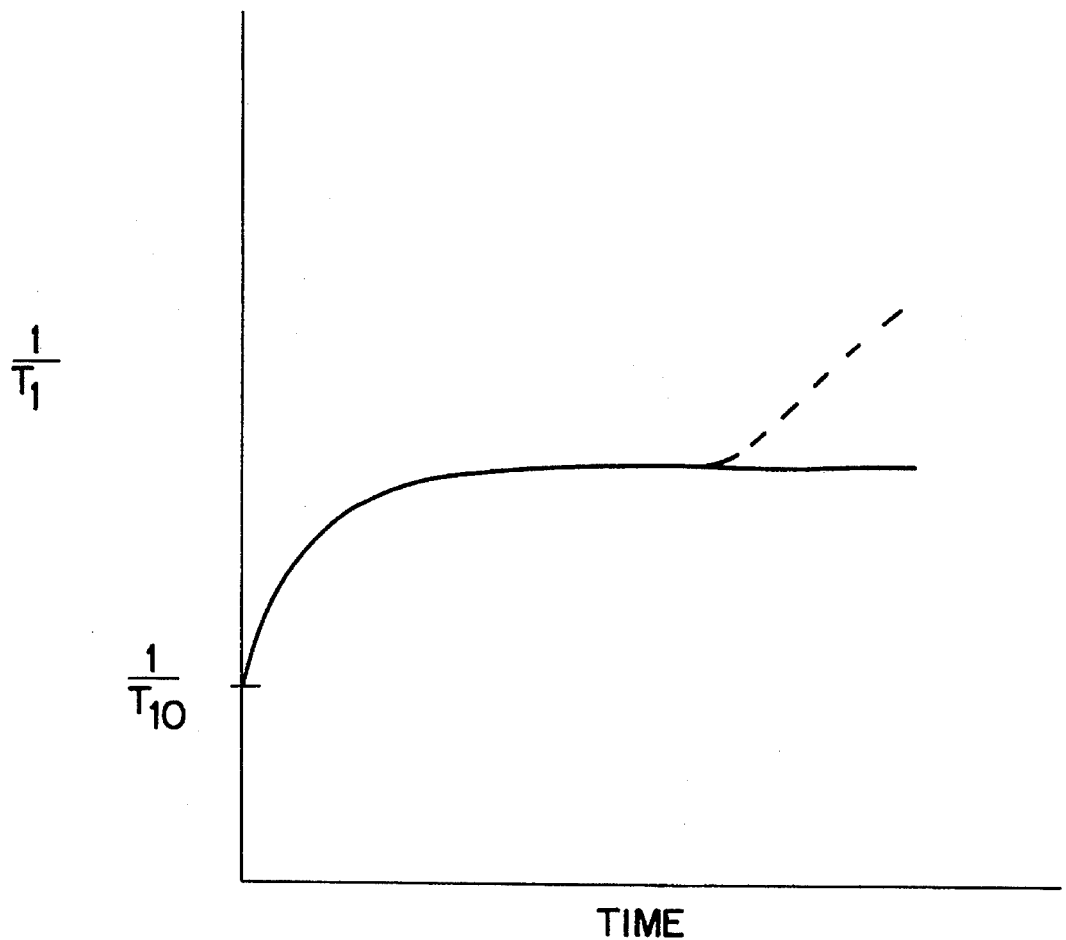
FIG. 4 shows the expected function of the inverse of relaxation time $T_1$ versus time for a patient administered a constant infusion of a renally excreted xenobiotic compound.

The method of the present invention may be used to monitor the kidney function of a patient, for example, following surgery, where renal deterioration or failure may occur. FIGS. 3 and 4 show the expected relationship between the inverse of the relaxation time $T_1$ versus time subsequent to either bolus injection (FIG. 3) or constant infusion (FIG. 4) of a renally excreted xenobiotic compound such as ProHance®. ($T_{10}$ denotes the value of $T_1$ prior to administration of the xenobiotic compound).

FIG. 3 illustrates that, where a bolus injection of the compound is employed, the measured value of $1/T_1$ will increase sharply and then decrease over time until reaching $T_{10}$ for a normal patient. When renal impairment (e.g. kidney failure) occurs, the value of $1/T_1$ will decrease more slowly or level off over time.

FIG. 4 illustrates that, where a constant infusion of the compound is employed, the measured value of $1/T_1$ will increase sharply, and will then become constant for a normal patient at steady state where the excretion rate equals the rate of infusion. When renal impairment (e.g. kidney failure) occurs, the value of $1/T_1$ will continue to increase over time.

What is claimed is:

1. A method for the non-spectroscopic, non-imaging determination in vivo of the concentration of an NMR-detectable, paramagnetic xenobiotic compound, comprising the steps of:

(a) recording one or more in vivo measurements of the intensity of a magnetic resonance (NMR) signal from said xenobiotic compound, without substantially varying the magnetic field strength or radiation energy frequency over time to obtain a spectrum and without substantially varying the magnetic field strength spatially to obtain an image, at a measurement site of a living subject by employing an NMR detection system which is capable of measuring the intensity of said signal and which is located at said measurement site; and (b) determining the concentration of said xenobiotic compound by a comparison of the signal intensity of said one or more measurements obtained in step (a) with the signal intensity of a standard.

2. The method of claim 1, wherein said xenobiotic compound is NMR-detectable by altering the signal from a compound which is endogenous to said subject and which possesses an NMR-detectable nucleus.

3. The method of claim 2, wherein said endogenous NMR-detectable nucleus is a water proton.

4. The method of claim 1, comprising the steps of:

(i) prior to administration of said xenobiotic compound, recording an in vivo measurement of the intensity of a magnetic resonance (NMR) signal from nuclei endogenous to a living subject, at a measurement site of said subject, by employing an NMR detection system which is capable of measuring the intensity of said signal and which is located at said measurement site;

(ii) administering said xenobiotic compound to said subject, wherein said compound is capable of altering the intensity of the NMR signal from said endogenous nuclei;

(iii) subsequent to said administration, recording an in vivo measurement of the intensity of the NMR signal from said endogenous nuclei, the latter having been altered by the presence of said xenobiotic compound, by employing said NMR detection system; and (iv) determining the concentration of said xenobiotic compound by a comparison of the measurement obtained in step (i) with the measurement obtained in step (iii).

5. The method of claim 1, comprising the steps of:

(i) administering said xenobiotic compound to a living subject, wherein said xenobiotic compound possesses an NMR-detectable nucleus per se or where said xenobiotic compound is capable of altering the intensity of a magnetic resonance (NMR) signal from nuclei endogenous to said subject;

(ii) subsequent to said administration, recording an in vivo measurement of the intensity of a magnetic resonance (NMR) signal generated by the NMR-detectable nuclei of said xenobiotic compound or generated by said endogenous nuclei, the latter having been altered by the presence of said xenobiotic compound, at a measurement site of said subject, by employing an NMR detection system which is capable of measuring the intensity of said signal and which is located at said measurement site;

(iii) thereafter, repeating step (ii) at least once at a time prior to complete clearance of said xenobiotic compound by excretion and/or metabolism from said subject; and (iv) determining the concentration of said xenobiotic compound, as a function of time, by a comparison of the measurement obtained in step (ii) with the measurement(s) obtained in step (iii).

6. The method of claim 1, wherein the intensity of said NMR signal is expressed as relaxation time $T_1$, relaxation time $T_2$, $T_{1\rho}$, $$\pi \prod_{i}^{n} I_z$$

(dipolar order), nuclei density or $K_n$.

7. The method of claim 1, wherein said measurement site is an arm, finger, toe or earlobe of a human subject.

8. The method of claim 3, wherein said xenobiotic compound is a paramagnetic contrast agent.

9. The method of claim 8, wherein sequential measurements are taken in step (a), and the status of the excretory organ(s) of the subject is determined in step (b) by comparing the change in signal intensity over time.

10. The method of claim 9, wherein said contrast agent is Gd-diethylenetriaminepentaacetic acid (Gd-DTPA), Gd-diethylenetriaminetriacetic acid bismethylamide (Gd-DTPA-BMA), Gd-tetraazacyclododecane tetraacetic acid (Gd-DOTA), or Gd-hydroxypropyl tetraazacylododecanetriacetic acid (Gd-HP-DO3A) (Pro-Hance®).

11. A method for the non-spectroscopic, non-imaging evaluation in vivo of the glomerular filtration functioning of a living subject, comprising the steps of:

(i) recording an in vivo measurement of the intensity of a magnetic resonance (NMR) signal from nuclei endogenous to said subject, at a measurement site of said subject, by employing an NMR detection system which is capable of measuring the intensity of said signal and which is located at said measurement site, and calculating $T_{10}$, where $T_{10}$ is the longitudinal relaxation time corresponding to said measurement;

(ii) thereafter, administering to said subject a renally excreted paramagnetic contrast agent which is capable of altering the intensity of the NMR signal from said endogenous nuclei;

(iii) subsequent to said administration, recording one or more in vivo measurements of the intensity of the NMR signal from said endogenous nuclei, the latter having been altered by the presence of said contrast agent, by employing said NMR detection system and, for each measurement so obtained, determining $T_1$, where $T_1$ is the longitudinal relaxation time corresponding to each said measurement;

(iv) calculating the halftime $T_{1/2}$ from said values $T_{10}$ and $T_1$; and (v) evaluating the glomerular filtration of said subject from the value $T_{1/2}$, wherein said measurements are obtained without substantially varying the magnetic field strength or radiation energy frequency over time to obtain a spectrum and without substantially varying the magnetic field strength spatially to obtain an image.

12. The method of claim 11, wherein said living subject is a human.

13. The method of claim 12, wherein said measurement site is remote from the kidneys of said subject.

14. The method of claim 13, wherein said measurement site is a finger, toe or earlobe of said subject.

15. A method for the in vivo determination of the clearance rate of an NMR-detectable, paramagnetic xenobiotic compound by one or more excretory organs of a living subject, comprising the steps of:

(a) recording one or more in vivo measurements of the intensity of a magnetic resonance (NMR) signal from said xenobiotic compound at a measurement site of said subject by employing an NMR detection system which is capable of measuring the intensity of said signal and which is located at a measurement site of said subject which is remote from said one or more excretory organs; and (b) determining the clearance rate of said xenobiotic compound by a comparison of the signal intensity of said one or more measurements obtained in step (a) with the signal intensity of a standard.

16. The method of claim 15, wherein said one or more organs are one or both kidneys of said subject, and wherein the functional status of said kidneys is determined by said clearance rate.

* * * * *